United States Patent [19]

Hashimoto et al.

[11] 4,220,548
[45] Sep. 2, 1980

[54] SHAMPOO COMPOSITION COMPRISING CALCIUM OR MAGNESIUM ANIONIC SURFACTANTS AND QUATERNARY NITROGEN-CONTAINING CELLULOSE ETHERS

[75] Inventors: Shigeru Hashimoto, Chiba; Tōru Ōno, Kasukabe, both of Japan

[73] Assignee: The Lion Fat and Oil Co., Ltd., Tokyo, Japan

[21] Appl. No.: 895,033

[22] Filed: Apr. 10, 1978

[30] Foreign Application Priority Data

Apr. 15, 1977 [JP] Japan .................................. 52-43198

[51] Int. Cl.$^2$ .......................... C11D 1/65; C11D 1/14; C11D 3/48
[52] U.S. Cl. .................................. 252/106; 252/545; 252/547; 252/548; 252/153; 252/550; 252/551; 252/554; 252/555; 252/558; 252/DIG. 2; 252/DIG. 13; 252/DIG. 14
[58] Field of Search ............... 252/547, 550, 551, 554, 252/555, 558, DIG. 2, DIG. 13, DIG. 14, 106, 545, 548; 424/70, 78

[56] References Cited

U.S. PATENT DOCUMENTS

| | | | |
|---|---|---|---|
| 3,580,853 | 5/1971 | Parran | 252/547 |
| 3,816,616 | 6/1974 | Anguillo et al. | 424/70 |
| 3,849,548 | 11/1974 | Grand | 424/70 |
| 3,876,760 | 4/1975 | Nersesian et al. | 424/70 |
| 3,928,251 | 12/1975 | Bolich et al. | 252/545 |
| 3,962,418 | 6/1976 | Birkofer | 424/70 |
| 3,964,500 | 6/1976 | Drakoff | 132/7 |
| 4,080,310 | 3/1978 | Guttler et al. | 252/544 |
| 4,101,456 | 7/1978 | Renaud et al. | 252/551 |
| 4,133,779 | 1/1979 | Hellyer et al. | 252/547 |

FOREIGN PATENT DOCUMENTS 2423833 12/1974 Fed. Rep. of Germany .
45-36590 11/1970 Japan .
46-143550 12/1971 Japan .

*Primary Examiner*—P. E. Willis, Jr.
*Attorney, Agent, or Firm*—Jesse B. Grove, Jr.

[57] ABSTRACT

A shampoo composition including from 3 to 50% by weight of one or more anionic surfactants and from 0.05 to 5% by weight of a quaternary nitrogen-containing cellulose ether having a predetermined quaternary nitrogen content, the anionic surfactants being selected from the group consisting of the compounds represented by the general formulas:

$$R\text{-}(OR')_n OSO_3 M_{\frac{1}{2}} \qquad (I),$$

$$R\text{-}SO_3 M_{\frac{1}{2}} \qquad (II),$$

and $$OS\text{-}M_{\frac{1}{2}} \qquad (III)$$

where R is an alkyl group having an average of from 8 to 18 carbon atoms or an alkylphenyl group substituted by alkyl groups having an average of from 6 to 15 carbon atoms, R' is an alkylene group having 2 or 3 carbon atoms, n is an integral number equal to from 0 to 6, OS is the acid radical of an anionic surfactant obtained by sulfonation of olefins having an average of from 10 to 18 carbon atoms, and M is a magnesium or calcium ion.

13 Claims, No Drawings

SHAMPOO COMPOSITION COMPRISING CALCIUM OR MAGNESIUM ANIONIC SURFACTANTS AND QUATERNARY NITROGEN-CONTAINING CELLULOSE ETHERS

BACKGROUND OF THE INVENTION

This invention relates to shampoo compositions useful in washing the hair and the scalp and combining excellent detergency and foaming power with good hair conditioning effects.

Conventional shampoo compositions have the disadvantage that, when they are used to wash the hair and the like, the fats and oils attached to the surfaces thereof tend to be removed to an undue extent. As a result of the undue removal of the fats and oils, the hair will feel loose and dry because of increased evaporation of moisture and may suffer damage on occasions of brushing. Moreover, the hair will make an ineffective response to a permanent wave set or hairsetting process, thus leading to a reduction in the so-called hair manageability.

As is evident from the above description, the degree of hair softening and the feel of hair lubricity are very much influenced by the amount of moisture contained in the hair. Thus, even if the moisture content of the hair equilibrated with atmospheric moisture is reduced by as little as 1%, the feel of the hair will enable one to detect the difference sensitively.

In washing the hair and the like, therefore, it has been of great interest to maintain the moisture content of the hair equilibrated with atmospheric moisture at an adequate level and thereby improve hair conditioning effects. For this purpose, a hair rinse, hair conditioner, hair cream containing a humectant, or the like is generally used after shampooing.

However, the use of such hair care preparations not only means a waste of money but requires extra time and labor. Meanwhile, several shampoo compositions have recently been developed which serve both to wash the hair and to produce hair conditioning effects.

One of such shampoo compositions has for its essential ingredients a water-soluble acid salt of a quaternary aminoalkyl ester of ethylenically unsaturated carboxylic acid polymer and an ampholytic surfactant.

However, repeated use of this shampoo composition may impair the appearance of the hair, so that it is not suitable for commercial applications.

Another shampoo composition has for its essential ingredients an anionic surfactant, zwitter-ionic surfactant, polyethoxylated nonionic surfactant, water, and quaternary nitrogen-containing cellulose ether.

Still another shampoo composition has for its essential ingredients a quaternary nitrogen-containing cellulose ether and an ampholytic or polar nonionic surfactant.

In brief, all of the above-described shampoo compositions comprise a combination of a quaternary nitrogen-containing polymeric compound and an ampholytic (including "zwitterionic" in a broad sense of the word) or polar nonionic surfactant. However, these shampoo compositions involve a number of problems. The surfactants used therein are less economical than commonly used alkyl ethoxysulfate (AES). Moreover, these shampoo composition tend to undergo a color change during storage. Furthermore, the purification of shampoo compositions containing an ampholytic surfactant requires meticulous care, which naturally leads to an increase in complexity of the manufacturing process and hence a rise in cost.

Summary of the Invention

This invention has been made for the purpose of providing a shampoo composition which solves the above-described problems of the prior art and has excellent shampoo properties. In accordance with this invention, there is provided a shampoo composition including from 3 to 50% by weight of at least one anionic surfactant selected from the group consisting of the compounds represented by the general formulas:

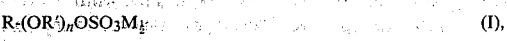    (I),

    (II), and

    (III)

where R is an alkyl group having an average of from 8 to 18 carbon atoms or an alkylphenyl group substituted by alkyl group having an average of from 6 to 15 carbon atoms, $R'$ is an alkylene group having 2 or 3 carbon atoms, n is an integral number equal to from 0 to 6, OS is the acid radicals of an anionic surfactant obtained by sulfonation of olefins having an average of from 10 to 18 carbon atoms, and M is a magnesium or calcium ion, and from 0.05 to 5% by weight of a quaternary nitrogen-containing cellulose ether having a quaternary nitrogen content of from 0.5 to 3.5% by weight.

When compared with prior art preparations, the shampoo composition of this invention has more excellent detergency and foaming power, produces better hair conditioning effects, and achieves more consistent quality and greater economy.

Detailed Description of the Preferred Embodiments

Since quaternary nitrogen-containing cellulose ethers are said to be capable of producing good hair conditioning effects, the inventors carried on intensive and extensive research concerning a large number of combinations of these cellulose ethers and various surfactants. Consequently, it was confirmed that, when combined with a quaternary nitrogen-containing cellulose ether as described above, commonly used surfactants such as the sodium and triethanolamine salts of alkyl ethoxysulfates, alkyl sulfates and the like failed to produce any appreciable hair conditioning effects. It was unexpectedly found, however, that the magnesium and calcium salts of anionic surfactants used in combination with a quaternary nitrogen-containing cellulose ether exhibited excellent shampoo properties such as detergency and foaming power, produced good hair conditioning effects, and achieved great economy. The present invention has been completed on the basis of this finding.

The shampoo composition of this invention includes from 3 to 50% by weight and preferably from 5 to 30% by weight of at least one anionic surfactant as previously defined and from 0.05 to 5% by weight and preferably from 0.1 to 4% by weight of a quaternary nitrogen-containing cellulose ether having a quaternary nitrogen content of from 0.5 to 3.5% by weight.

The anionic surfactant which is used as one of the essential ingredients in the shampoo composition of this invention can be represented by any of the general formulas:

$$R-(OR')_n OSO_3 M_{\frac{1}{i}} \qquad (I),$$

$$R-SO_3 M_{\frac{1}{i}} \qquad (II),$$

and $$OS-M_{\frac{1}{i}} \qquad (III)$$

where R, R', n, OS and M are as previously defined.

The anionic surfactants represented by these general formulas are more specifically described below.

Preferred examples of the compounds represented by the general formula (I) are the magnesium and/or calcium salts sulfuric acid ester of natural lauryl alcohol substituted by 1–5 mole ethoxy, of, $C_{11}$ to $C_{15}$ aliphatic alcohols substituted by 1–5 mole ethoxy, of, $C_{12}$ to $C_{13}$ aliphatic alcohols substituted by 1–2 mole ethoxy, of of $C_{11}$ to $C_{15}$ aliphatic alcohols, and of $C_{12}$ to $C_{13}$ aliphatic alcohols (for example, these derivatives of aliphatic alcohols are synthesized by the oxo process).

Preferred examples of the compounds represented by the general formula (II) are the magnesium and/or calcium salts of $C_{12}$ to $C_{14}$ alkyl sulfonic acids and $C_{11}$ to $C_{13}$ alkyl benzene sulfonic acid.

Preferred examples of the compounds represented by the general formula (III) are the magnesium and/or calcium salts of anionic surfactants obtained by sulfonating $C_{12-14}$ alphaolefins, $C_{12-16}$ vinylidene-olefins, or $C_{12-16}$ inner-olefins (for example, those made by the wax-cracking process, the ethylene polymerization process using a Ziegler catalyst, or modifications of these processes) with sulfur trioxide and the like and then hydrolyzing the product.

The quaternary nitrogen-containing cellulose ether which is used as the other essential ingredient in the shampoo composition of this invention is a compound represented by the structural formula:

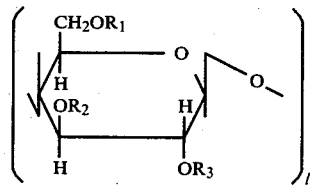

where $R_1$, $R_2$ and $R_3$ are hydrogen atoms or substituent groups of the formula:

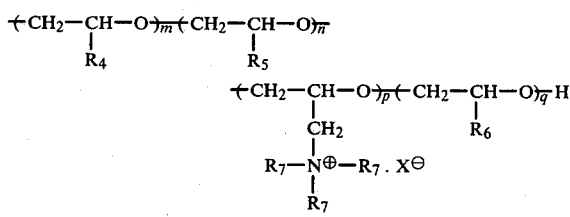

and $R_4$, $R_5$, $R_6$, $R_7$, m, n, p and q in one substituent group may be different from those in another substituent group; m, n and q are integral numbers equal to from 0 to 10; p is an integral number equal to from 0 to 3; $R_4$, $R_5$ and $R_6$ are hydrogen atoms or methyl groups; $R_7$ is a methyl, ethyl or propyl group; X is a halogen atom; and l is a number equal to from 100 to 20,000. The sum of (m+n+q) has an average value of from 1 to 3 per glucose unit and p has an average value of from about 0.1 to about 0.8 and preferably from about 0.2 to about 0.5 per glucose unit. The nitrogen content of the quaternary nitrogen-containing cellulose ether is correlated with the average value of p. Thus, the former is 0.5% by weight when the latter is about 0.1 and the former is 3.5% by weight when the latter is about 0.8.

Preferred examples of the quaternary nitrogen-containing cellulose ether used in the shampoo composition of this invention are Polymer JR-125 (having a viscosity of 60–150 cps at 25° C.), Polymer JR-400 (having a viscosity of 300–500 cps at 25° C.), and Polymer JR-30M (having a viscosity of 1,000–2,500 cps at 25° C.), all manufactured and sold by Union Carbide Co. The most preferred example is the compound obtained by effecting the addition of ethylene oxide to cellulose (cellulose has two glucose units for its repeating structural unit) and then reacting the resultant hydroxyethyl cellulose with glycidyltrimethylammonium chloride. In the addition step, ethylene oxide is used in an amount equal to from 1 to 3 moles per glucose unit. The hydroxyethyl cellulose obtained by the addition of ethylene oxide to cellulose is reacted with glycidyltrimethylammonium chloride so that the degree of substitution of quaternary nitrogen-containing groups is from about 0.1 to about 0.8 and preferably from about 0.2 to about 0.5 per glucose unit.

The amount of the anionic surfactant present in the shampoo composition of this invention may vary from 3 to 50% by weight and preferably from 5 to 30% by weight. If it is less than 3% by weight, the shampoo composition will be inferior in foraming power, while if it is greater than 50% by weight, the shampoo composition stored under low-temperature conditions (for example, in cold districts or in the winter season) will become turbid or separate into two layers so as to diminish its commercial value.

The amount of the quaternary nitrogen-containing cellulose ether in the shampoo compositions of this invention may vary from 0.05 to 5% by weight and preferably from 0.1 to 4% by weight. If it is less than 0.05% by weight, the shampoo composition will fail to produce satisfactory hair conditioning effects, while if it is greater than 5% by weight, the shampoo composition will undesirably impart a sticky feel to the hair after rinsing.

In addition to the above-described essential ingredients, various ingredients commonly used in shampoo preparations, such as fatty alkylolamides, ethylene glycol distearate, solvents, perfumes, bactericides, chelating agents, ultraviolet absorbers, and the like, may be included in the shampoo composition of this invention.

Furthermore, an ampholytic surfactant may be optionally included in the shampoo composition of this invention. However, it is preferably used in an amount less than 0.5 part by weight per part by weight of the anionic surfactant defined in this invention (i.e. less than 50% by weight based on the weight of the latter).

Besides the anionic surfactant defined in this invention, conventional anionic surfactants of the alkali metal salt type, triethanolamine salt type, and other types may be optionally included in the shampoo composition of this invention. However, they are preferably used in an amount less than 2 parts by weight per part by weight of the anionic surfactant defined in this invention (i.e. less than 200% by weight based on the weight of the latter), and more preferably used in an amount less than 1 part by weight per part by weight of the latter.

When the shampoo composition of this invention is used to wash the hair, hair conditioning is achieved at the same time and the moisture content of the hair equilibrated with atmospheric moisture is thereby enhanced. Thus, aftercare may be omitted so as to allow a saving of money and labor.

In contract to prior art shampoo composition using a quaternary nitrogen-containing cellulose ether, the shampoo composition of this invention remarkably increases the amount of quaternary nitrogen-containing cellulose ether attached to the hair and imparts softness, lubricity, gloss, easiness of combing, and the like to the hair, indicating that it is far superior in hair conditioning effects to prior art ones. Moreover, repeated use of the shampoo composition of this invention does not cause any excessive accumulation thereof on the hair, but gives a moist feel and an excellent appearance to the hair. Accordingly, if it is desired to produce hair conditioning effects equivalent to those achievable with prior art shampoo compositions, the expected results can be obtained by using the shampoo composition of this invention at lower concentrations.

The shampoo composition also decreases entanglement and raspiness of the hair on the occasion of washing and rinsing, exhibits excellent foaming power, and has little possibility of undergoing a change in color and properties during storage. Furthermore, anionic surfactants used as one of the essential ingredients are more desirable than ampholytic surfactants from the practical viewpoints of price and purification requirements.

Besides the above-described effects, the shampoo composition of this invention has the following additional effects. When its pH is adjusted to a weakly acidic region of from 3 to 5, the shampoo composition of this invention can produce good hair conditioning effects. This is a great advantage from a practical point of view, because prior art shampoo composition comprising an ampholytic surfactant and a quaternary nitrogen-containing cellulose ether have their optimal pH restricted to the vicinity of neutrality and fail to produce satisfactory hair conditioning effects in the weakly acidic region. In addition, when a quaternary nitrogen-containing cellulose ether having cationic charge is used in combination with an anionic surfactant as previously defined, the former forms a complex salt with the latter. Then, a film of this complex salt attaches to the surfaces of hair filaments so strongly as to resist repeated rinsing with water. This is considered to be the reason why the shampoo composition of this invention increases the moisture content of the hair and thereby produces good hair conditioning effects. There is the generally accepted idea that such results can be achieved solely by the combination of a quaternary nitrogen-containing cellulose ether and an ampholytic or polar nonionic surfactant. The present invention has destroyed this idea by providing a novel shampoo composition comprising a quaternary nitrogen-containing cellulose ether and the specific anionic surfactant and exhibiting for more excellent shampoo properties than prior art shampoo compositions.

The present invention is further illustrated by the following examples. First of all, the procedures employed therein for the physical and organoleptic evaluation of shampoo properties are explained below.

(1) Foaming power

Using a sample with a concentration of 6%, the height (in mm) of the foam produced by the Ross-Miles method was measured at a temperature of 20° C.

(2) Adsorption of complex salt of quaternary nitrogen-containing cellulose ether (hereinafter referred to as "cationic cellulose ether derivative")

A bundle of hair was washed with a shampoo composition containing a tritium-labeled cationic cellulose ether derivative and the amount of the derivative adsorbed on the surfaces of the hair was determined by means of a scintillation counter.

(3) Moisture content of hair

A bundle of hair was washed with a 6% aqueous solution of a shampoo composition to be tested, rinsed with water, air-dried, and then stored in an atmosphere having a temperature of 25° C. and a relative humidity of 65% until equilibrium was established. Thereafter, the moisture content of the hair was determined by means of a moisture analyzer.

(4) Degree of hair softening (by organoleptic evaluation)

Bundles of hair were washed with a shampoo composition to be tested or a commercially available preparation, rinsed with water, and then dried. Using pair comparison tables, the degree of hair softening was evaluated by 20 testers. The results were rated as follows:

| Rating | Definition |
| --- | --- |
| + | Superior to the commercially available preparation. |
| + | Slightly superior to the commercially available preparation. |
| ± | Equivalent to the commercially available preparation. |

(5) Hair manageability

Hair manageability was organoleptically evaluated in the same manner as for the degree of hair softening.

(6) Kinetic friction coefficient of hair

A bundle of hair was washed with a 6% aqueous solution of a shampoo composition to be tested, rinsed with water, and then air-dried. Thereafter, the kinetic friction coefficient of the hair was measured by means of a friction coefficient meter.

(7) Degree of hair combing

The easiness of hair combing after rinsing and after drying was organoleptically evaluated in the same manner as for the degree of hair softening.

(8) Degree of color change

The absorbance of a shampoo composition to be tested was measured at a maximum wavelength of 420 m$\mu$. Then, two samples of the shampoo composition were charged into bottles made of polyvinyl chloride. One of them was allowed to stand at a temperature of 45° C. for a period of b 1 month, while the other was allowed to stand under outdoor conditions for a period of 1 month. Thereafter, the absorbance of each sample was measured in the same manner as before and the degree of color change was calculated according to the following equation.

Degree of Color Change (%) = $I_t - I_o/I_o \times 100$ where $I_o$ denotes the initial absorbance and $I_t$ denotes the absorbance measured after the sample was allowed to stand for 1 month.

EXAMPLES 1-5 AND CONTROLS 1-2

Five shampoo compositions of this invention comprising the ingredients shown in Table 1 and containing a cationic cellulose ether derivative in varying amounts were subjected to a series of tests for shampoo properties as listed in Table 1. The results are summarized in Table 1. For purposes of comparison, two shampoo compositions (Controls 1 and 2) in which the amount of the cationic cellulose ether derivative is less than the lower limit or greater than the upper limit were subjected to the same tests. The results are also summarized in Table 1.

composition (Control 1) containing 0.03% by weight of the derivative did not differ from a commercially available preparation, and the shampoo composition (Control 2) containing 6% by weight of the derivative undesirably imparted stickiness and stiffness to the hair.

EXAMPLE 6 AND CONTROLS 3-6

A shampoo composition of this invention comprising the ingredients shown in Table 2 was subjected to a series of tests for shampoo properties as listed in Table 2. The results are summarized in Table 2. For purposes of comparison, four shampoo compositions (Controls 3-6) containing the Na, K, Li and TEA (triethanolamine) salts of LES respectively were subjected to the same tests. The results are also summarized in Table 2.

Table 2

|  |  | Example 6 | Control 3 | Control 4 | Control 5 | Control 6 |
|---|---|---|---|---|---|---|
| Composition (% by weight) | Cationic Cellulose Ether Derivative (A) | 1.0 | 1.0 | 1.0 | 1.0 | 1.0 |
| | LES-Ca½ | 15.0 | — | — | — | — |
| | LES-Na | — | 15.0 | — | — | — |
| | LES-K | — | — | 15.0 | — | — |
| | LES-Li | — | — | — | 15.0 | — |
| | LES-TEA | — | — | — | — | 15.0 |
| | Water | 84.0 | 84.0 | 84.0 | 84.0 | 84.0 |
| Tests | Foaming Power (mm) | 155 | 130 | 130 | 130 | 130 |
| | Adsorption of Complex Salt of Cationic Cellulose Ether Derivative (μg/mg hair) | 7.0 | 0.1 | 0.1 | 0.1 | 0.1 |
| | Moisture Content of Hair (%) | 13.0 | 7.0 | 7.0 | 7.0 | 7.0 |
| | Degree of Hair Softening | ++ | ± | ± | ± | ± |
| | Hair Manageability | ++ | ± | ± | ± | ± |
| | Kinetic Friction Coefficient of Hair | 0.2 | 0.8 | 0.8 | 0.8 | 0.8 |
| | Degree of Hair Combing (after rinsing) | ++ | ± | ± | ± | ± |
| | Degree of Hair Combing (after drying) | ++ | ± | ± | ± | ± |

As can be seen from the test results shown in Table 2, only the shampoo composition containing the Ca salt of an anionic surfactant produced good hair conditioning effects, and the shampoo compositions (Controls 3-6) containing the Na, K, Li and TEA salts of the anionic Table 1

|  |  | Control 1 | Example 1 | Example 2 | Example 3 | Example 4 | Example 5 | Control 2 |
|---|---|---|---|---|---|---|---|---|
| Composition (% by weight) | Cationic Cellulose Ether Derivative (A) *1 | 0.03 | 0.05 | 0.1 | 1.0 | 3.0 | 5.0 | 6.0 |
| | LES-Mg½ *2 | 15.0 | 15.0 | 15.0 | 15.0 | 15.0 | 15.0 | 15.0 |
| | Water | 84.97 | 84.95 | 84.9 | 84.0 | 82.0 | 80.0 | 79.0 |
| Tests | Foaming Power (mm) | 140 | 140 | 150 | 160 | 170 | 170 | 170 |
| | Adsorption of Complex Salt of Cationic Cellulose Ether Derivative (μg/mg hair) | 0.1 | 1.0 | 5.0 | 7.0 | 10.0 | 15.0 | 20.0 |
| | Moisture Content of Hair (%) | 7.0 | 11.0 | 12.5 | 13.5 | 15.0 | 17.0 | 17.0 |
| | Degree of Hair Softening | ± | + | ++ | ++ | ++ | ++ | ± *3 |
| | Hair Manageability | ± | + | ++ | ++ | ++ | ++ | ± |
| | Kinetic Friction Coefficient of Hair | 0.7 | 0.4 | 0.2 | 0.2 | 0.2 | 0.2 | 0.2 |
| | Degree of Hair Combing (after rinsing) | ± | + | ++ | ++ | ++ | ++ | ++ *4 |
| | Degree of Hair Combing (after drying) | ± | + | ++ | ++ | ++ | ++ | ++ |

*1 Polymer JR-400 (the trade name for a commercial product of Union Carbide Co.) was used.
*2 LES- represents the acid radicals of $C_{12}$ to $C_{13}$ aliphatic alcohols 3 mole ethoxy sulfates synthesized by the oxo process.
*3 Stiffness was caused.
*4 Stickiness was caused.

As can be seen from the test results shown in Table 1, good hair conditioning effects were produced when the amount of the cationic cellulose ether derivative was in the range of from 0.05 to 5% by weight. The shampoo surfactant failed to produce satisfactory hair conditioning effects.

EXAMPLES 7–10 AND CONTROLS 7–8

Four shampoo compositions of this invention comprising the ingredients shown in Table 3 were subjected to a series of tests for shampoo properties as listed in Table 3. The results are summarized in Table 3. For purposes of comparison, two shampoo compositions (Controls 7–8) containing a conventional ampholytic surfactant were subjected to the same tests. The results are also summarized in Table 3.

EXAMPLES 11–14 AND CONTROLS 9–11

Four shampoo compositions of this invention comprising the ingredients shown in Table 4 were subjected to color change tests. The results are summarized in Table 4. For purposes of comparison, three shampoo compositions (Controls 9, 11 and 10) containing Miranol C2M and $C_{12}$-alkyldimethylamine oxide respectively were subjected to the same tests. The results are also summarized in Table 4.

Table 3

|  |  | Control 7 | Control 8 | Example 7 | Example 8 | Example 9 | Example 10 |
|---|---|---|---|---|---|---|---|
| Composition (% by weight) | Cationic Cellulose Ether Derivative (A) | 1.0 | 1.0 | 1.0 | 1.0 | 1.0 | 1.0 |
|  | Miranol C2M Conc. *1 | 15.0 | 10.0 | — | — | — | — |
|  | LES-Na | — | 5.0 | — | — | — | — |
|  | LES-Mg$_\frac{1}{2}$ | — | — | 15.0 | — | — | — |
|  | AS-Mg$_\frac{1}{2}$ *2 | — | — | — | 15.0 | — | — |
|  | PS-Mg$_\frac{1}{2}$ *3 | — | — | — | — | 15.0 | — |
|  | AOS-Mg$_\frac{1}{2}$ *4 | — | — | — | — | — | 15.0 |
|  | Water | 84.0 | 84.0 | 84.0 | 84.0 | 84.0 | 84.0 |
| Tests | Foaming Power (mm) | 90 | 110 | 160 | 165 | 160 | 160 |
|  | Adsorption of Complex Salt of Cationic Cellulose Ether Derivative (μg/mg hair) | 2.0 | 1.0 | 7.0 | 6.5 | 6.0 | 6.0 |
|  | Moisture Content of Hair (%) | 11.5 | 11.0 | 13.5 | 13.0 | 13.0 | 13.0 |
|  | Degree of Hair Softening | + | + | ++ | ++ | ++ | ++ |
|  | Hair Manageability | + | + | ++ | ++ | ++ | ++ |
|  | Kinetic Friction Coefficient of Hair | 0.3 | 0.4 | 0.2 | 0.2 | 0.2 | 0.2 |
|  | Degree of Hair Combing | + | + | ++ | ++ | ++ | ++ |

*1 Miranol C2M (the trade name for a commercial product of Miranol Co.) is the compound represented by the structural formula:

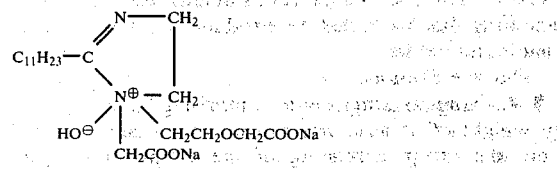

*2 AS-represents the acid radicals of sulfates of $C_{12}$ to $C_{15}$ aliphatic alcohols synthesized by the oxo process.
*3 PS-represents the $C_{12}$ to $C_{14}$ alkyl sulfonic acid radicals.
*4 AOS-represents the acid radical of the surfactant obtained by sulfonating $C_{12-14}$ alpha-olefins with sulfur trioxide and then hydrolyzing the product.

Table 4

|  |  | Control 9 | Example 11 | Example 12 | Example 13 | Example 14 | Control 10 | Control 11 |
|---|---|---|---|---|---|---|---|---|
| Composition (% by weight) | Cationic Cellulose Ether Derivative (A) | 1.0 | 1.0 | 1.0 | 1.0 | 1.0 | 1.0 | 1.0 |
|  | Miranol C2M Conc. | 15.0 | — | — | — | — | — | 10 |
|  | $C_{12}$-Alkyldimethylamine Oxide | — | — | — | — | — | 15.0 | — |
|  | LES-Na | — | — | — | — | — | — | 5 |
|  | LES-Mg$_\frac{1}{2}$ | — | 15.0 | — | — | — | — | — |
|  | AS-Mg$_\frac{1}{2}$ | — | — | 15.0 | — | — | — | — |
|  | PS-Mg$_\frac{1}{2}$ | — | — | — | 15.0 | — | — | — |
|  | AOS-Mg$_\frac{1}{2}$ | — | — | — | — | 15.0 | — | — |
|  | Water | 84.0 | 84.0 | 84.0 | 84.0 | 84.0 | 84.0 | 84.0 |
| Tests | Degree of Color Change (after outdoor exposure for 1 month) | 30 | 0 | 0 | 0 | 0 | 20 | 15 |
|  | Degree of Color Change (after exposure to 45° C. temperature for 1 month) | 90 | 2.0 | 3.0 | 3.0 | 5.0 | 85 | 65 |

As can be seen from the test results shown in Table 3, all the shampoo compositions containing the Mg salts of anionic surfactants exhibited excellent foaming power and produced good hair conditioning effects. Their foaming power and hair conditioning effects were superior to those of the shampoo compositions containing a conventional ampholytic surfactant.

As can be seen from the test results shown in Table 4, the shampoo compositions (Controls 9, 11 and 10) containing Miranol C2M and $C_{12}$-alkyldimethylamine oxide respectively presented a high degree of color change as a result of the outdoor and high-temperature exposure tests, which diminishes their commercial value. In contrast, the shampoo compositions of this invention produced little color change, indicating its remarkable stability to aging.

EXAMPLES 15-20

Six shampoo compositions of this invention comprising the ingredients shown in Table 5 were subjected to a series of tests for shampoo properties as listed in Table 5. The results are summarized in Table 5.

Table 5

|  |  | Example 15 | Example 16 | Example 17 | Example 18 | Example 19 | Example 20 |
|---|---|---|---|---|---|---|---|
|  | Cationic Cellulose Ether Derivative (A) | 1.0 | 1.0 | — | — | — | — |
|  | Cationic Cellulose Ether Derivative (B) *1 | — | — | 1.0 | 0.2 | — | — |
|  | Cationic Cellulose Ether Derivative (C) *2 | — | — | — | — | 0.2 | 1.0 |
| Composition | LES-Mg$_{\frac{1}{2}}$ | 50.0 | 30.0 | 20.0 | — | 10.0 | — |
| (% by | LAS-Mg$_{\frac{1}{2}}$ *3 | — | — | — | 10.0 | — | 5.0 |
| weight) | Diethanolamide of Coconut Oil Fatty Acid | 3.0 | 3.0 | 3.0 | 3.0 | 3.0 | 3.0 |
|  | Ethanol | 5.0 | 3.0 | — | 5.0 | — | 3.0 |
|  | Perfume | 0.3 | 0.3 | 0.3 | 0.3 | 0.3 | 0.3 |
|  | Water | 35.7 | 60.7 | 75.7 | 80.7 | 85.7 | 87.7 |
| pH |  | 7 | 4 | 7 | 5 | 5 | 5 |
|  | Degree of Hair Softening | ++ | ++ | ++ | ++ | ++ | ++ |
|  | Hair Manageability | ++ | ++ | ++ | ++ | ++ | ++ |
| Tests | Degree of Hair Combing (after rinsing) | ++ | ++ | ++ | ++ | ++ | ++ |
|  | Degree of Hair Combing (after drying) | ++ | ++ | ++ | ++ | ++ | ++ |

*1 Polymer JR-125 (the trade name for a commercial product of Union Carbide Co.) was used.
*2 Polymer JR-30M (the trade name for a commercial product of Union Carbide Co.) was used.
*3 LAS-represents the C$_{12}$ (av.) alkyl benzene sulfonic acid radical.

As can be seen from the test results shown in Table 5, all the shampoo compositions of these examples combine excellent shampoo properties with good hair conditioning effects.

EXAMPLE 21 AND CONTROLS 12-14

A shampoo composition of this invention comprising the ingredients shown in Table 6 were subjected to a series of tests for shampoo properties as listed in Table 6. The results are summarized in Table 6. For purposes of comparison, a shampoo composition (Control 12) containing a quaternary nitrogen-containing vinylpyrrolidone copolymer and two shampoo compositions (Controls 13 and 14) having AS-Mg$_{\frac{1}{2}}$ replaced by AS-Na were subjected to the same tests. The results are also summarized in Table 6.

As can be seen from the test results shown in Table 6, only the shampoo composition containing a cationic cellulose ether derivative and the Mg salt of an anionic surfactant produced good hair conditioning effects. The shampoo composition (Control 12) containing a quaternary nitrogen-containing vinylpyrrolidone copolymer and the shampoo compositions (Controls 13 and 14) including AS-Na failed to produce satisfactory hair conditioning effects.

What we claim is:

1. A shampoo composition comprising from 3 to 50% by weight of at least one anionic surfactant, selected from the group consisting of the compounds represented by the formulas:

$$R\text{-}(OR')_n OSO_3 M_{\frac{1}{2}} \qquad (I),$$

$$R\text{-}SO_3 M_{\frac{1}{2}} \qquad (II),$$

and $$OS\text{-}M_{\frac{1}{2}} \qquad (III)$$

Table 6

|  |  | Example 21 | Control 12 | Control 13 | Control 14 |
|---|---|---|---|---|---|
|  | Cationic Cellulose Ether Derivative (B) | 2.0 | — | 1.0 | — |
|  | Gafquart 755 *1 | — | 2.0 | — | 1.0 |
|  | AS-Mg$_{\frac{1}{2}}$ | 15.0 | 15.0 | — | — |
| Composition | AS-Na | — | — | 15.0 | 15.0 |
| (% by | Diethanolamide of Coconut |  |  |  |  |
| weight) | Oil Fatty Acid | 3.0 | 3.0 | 3.0 | 3.0 |
|  | Ethanol | 3.0 | 3.0 | 3.0 | 3.0 |
|  | Calcium Acetate | — | — | 0.5 | 0.5 |
|  | EDTA-2Na | 0.1 | 0.1 | 0.1 | 0.1 |
|  | Perfume | 0.3 | 0.3 | 0.3 | 0.3 |
|  | Water | 76.6 | 76.6 | 77.1 | 77.1 |
| pH |  | 7 | 7 | 7 | 7 |
|  | Degree of Hair Softening | ++ | ± | ± | ± |
|  | Hair Manageability | ++ | ± | ± | ± |
| Tests | Degree of Hair Combing (after rinsing) | ++ | + | ± | ± |
|  | Degree of Hair Combing (after drying) | ++ | ± | ± | ± |

*1 Quaternary Nitrogen-Containing Vinylpyrrolidone Copolymer (the trade name for a commercial product of GAF Co.) was used in an amount equal to 2.0 or 1.0% by weight as solid content.

wherein R is an alkyl group having an average of from 8 to 18 carbon atoms or an alkylphenyl group substituted by alkyl groups having an average of from 6 to 15 carbon atoms, R' is an alkylene group having 2 or 3 carbon atoms, n is an integral number equal to from 0 to 6, OS is the acid radical of an anionic surfactant obtained by sulfonation of olefins having an average of from 10 to 18 carbon atoms, and M is a magnesium or calcium ion; and from 0.05 to 5% by weight of a quarternary nitrogen-containing cellulose ether having a quarternary nitrogen content of from 0.5 to 3.5% by weight which is a compound represented by the general formula:

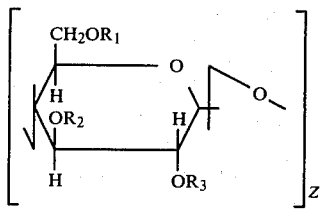

where $R_1$, $R_2'$ and $R_3$ each are hydrogen or a substituent group of the formula:

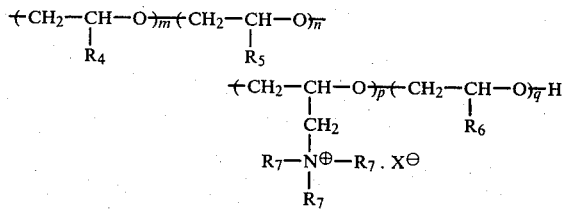

wherein $R_4$, $R_5$, $R_6$, $R_7$, m, n, p and q in one substituent group may be different from those in another substituent group; m, n and q are integral numbers of from 0 to 10; p is an integral number of from 0 to 3; $R_4$, $R_5$ and $R_6$ are hydrogen atoms or methyl groups, $R_7$ is a methyl, ethyl or propyl; X is a halogen atom; and Z is a number of from 100 to 20,000; and the sum of (m+n+q) has an average value of from 1 to 3 per glucose unit and p has an average value of from about 0.1 to 0.8 per glucose unit.

2. The shampoo composition as claimed in claim 1 wherein the anionic surfactant represented by the formula (I) is at least one member selected from the group consisting of the magnesium and calcium salts of sulfuric acid esters of lauryl alcohol substituted by 1-5 mole ethoxy, of $C_{11}$ to $C_{15}$ aliphatic alcohols substituted by 1-5 mole ethoxy, of $C_{12}$ to $C_{13}$ aliphatic alcohols substituted by 1-2 mole ethoxy of $C_{11}$ to $C_{15}$ aliphatic alcohols, and of $C_{12}$ to $C_{13}$ aliphatic alcohols.

3. A shampoo composition as claimed in claim 1 wherein the anionic surfactant represented by the general formula (II) is at least one member selected from the group consisting of the magnesium and calcium salts of $C_{12}$ to $C_{14}$ alkyl sulfonic acids and $C_{11}$ to $C_{13}$ alkyl benzene sulfonic acids.

4. A shampoo compositon as claimed in claim 1 wherein the anionic surfactant represented by the general formula (III) is at least one member selected from the group consisting of the magnesium and calcium salts of anionic surfactants obtained by sulfonating $C_{12-14}$ alpha-olefins, $C_{12-16}$ vinylidene-olefins, or $C_{12-16}$ inner-olefins and then hydrolyzing the product.

5. A shampoo composition as claimed in claim 1 wherein the quarternary nitrogen-containing cellulose ether having a quaternary nitrogen content of from 0.5 to 3.5% by weight is a compound represented by the general formula:

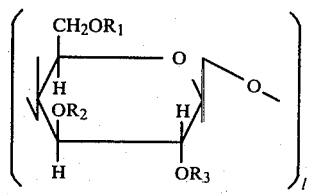

where $R_1$, $R_2$ and $R_3$ are hydrogen atmos or substituent groups of the formula:

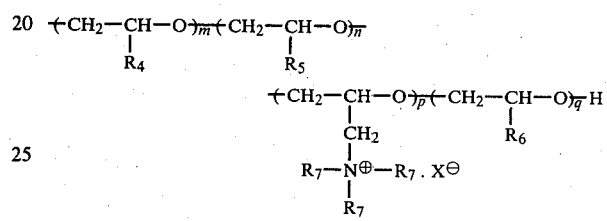

and $R_4$, $R_5$, $R_6$, $R_7$, m, n, p and q in one substituent group may be different from those in another substituent group; m, n and q are integral numbers equal to form 0 to 10; p is an integral number equal to from 0 to 3; $R_4$, $R_5$ and $R_6$ are hydrogen atoms or methyl groups; $R_7$ is a methyl, ethyl or propyl group; X is a halogen atom; and l is a number equal to from 100 to 20,000; and the sum of (m+n+q) has an average value of from 1 to 3 per glucose unit and p has an average value of from about 0.1 to 0.8 per glucose unit.

6. A shampoo composition as claimed in claim 1 wherein the quaternary nitrogen-containing cellulose ether having a quaternary nitrogen content of from 0.5 to 3.5% by weight is the compound obtained by effecting the addition of ethylene oxide to cellulose in an amount equal to from 1 to 3 moles per glucose unit and then reacting the resultant hydroxyethyl cellulose with glycidyltrimethylammonium chloride.

7. A shampoo composition as claimed in claim 1 further including an ampholytic surfactant.

8. A shampoo composition as claimed in claim 7 wherein the ampholytic surfactant is present in an amount less than 50% by weight based on the weight of the anionic surfactant.

9. The shampoo composition as claimed in claim 1 further including an anionic surfactant selected from the group consisting of alkali metal salts, triethanolamine salts and mixtures thereof.

10. A shampoo composition as claimed in claim 9 wherein the conventional anionic surfactant is present in an amount less than 200% by weight based on the weight of the anionic surfactant represented by way of the general formulas (I), (II) and (III).

11. A shampoo composition as claimed in claim 1 further including commonly used ingredients selected from the group consisting of fatty alkylolamides, ethylene glycol distearate, solvents, perfumes, bactericides, chelating agents, and ultraviolet absorbers.

12. A shampoo composition as claimed in claim 1 wherein said composition has pH adjusted to a value in the range of from 3 to 5.

13. A shampoo composition as claimed in claim 1 wherein the anionic surfactant represented by any of the general formulas (I), (II) and (III) is present in an amount equal to from 5 to 30% by weight and the quaternary nitrogen-containing cellulose ether having a quaternary nitrogen content of from 0.5 to 3.5% by weight is present in an amount equal to from 0.1 to 4% by weight.

* * * * *